United States Patent [19]

Dake et al.

[11] Patent Number: 5,199,939
[45] Date of Patent: Apr. 6, 1993

[54] RADIOACTIVE CATHETER

[76] Inventors: Michael D. Dake, 1915 Mandeville Canyon Rd., Los Angeles, Calif. 90049; Bruce Hedger, 16220 Gundry Ave., Paramount, Calif. 90723; Stephen Oesterle, 101 Burlingame Ave., Los Angeles, Calif. 90049

[21] Appl. No.: 484,117
[22] Filed: Feb. 23, 1990
[51] Int. Cl.$^5$ .............................................. A61N 5/00
[52] U.S. Cl. ......................................... 600/3; 600/8; 128/659
[58] Field of Search ........................................ 600/1–8; 128/656–659

[56] References Cited

U.S. PATENT DOCUMENTS

| | | | |
|---|---|---|---|
| 3,324,847 | 6/1967 | Zoumboulis | 128/1.2 |
| 3,674,006 | 7/1972 | Holmer | 600/7 |
| 3,872,856 | 3/1975 | Clayton | 128/1.2 |
| 4,096,862 | 6/1978 | DeLuca | 128/348 |
| 4,385,635 | 5/1983 | Ruiz | 128/658 |
| 4,578,061 | 3/1986 | Lemelson | 604/164 |
| 4,588,395 | 5/1986 | Lemelson | 604/39 |
| 4,706,652 | 11/1987 | Horowitz | 128/1.2 |
| 4,815,449 | 3/1989 | Horowitz | 600/8 |
| 4,819,618 | 4/1989 | Liprie | 600/7 |
| 4,842,590 | 6/1989 | Tanabe et al. | 128/656 |
| 4,861,520 | 8/1989 | van't Hooft et al. | 600/8 |
| 5,059,166 | 10/1991 | Fischell et al. | 600/3 |

OTHER PUBLICATIONS

McCormick et al., "Breast Cancer", *Interstitial Brachytherapy*, Raven Press Ltd., New York, 1990, pp. 221–225.
Breast Cancer, McCormick, et al., Interstitial Brachytherapy, Institial Collaborative Working Group, Raven Press, Ltd., N.Y. 1990.
Combination of External and Interstitial Irradiation in the Primary Management of Breast Carcinoma, Syed, et al., Cancer, vol. 46, No. 6, Sep. 15, 1980.
Intraluminal Irradiation in the Treatment of Esophageal Cancer, Syed, et al., Dept. of Rad. Oncol., Mem. Med. Center Mar. 18, 1987.
Mechanism of Angioplasty and Its Relation to Restenosis, Faxon, et al., Am. J. Cardiol. 1987:60-5B-9B.
Role of Ionizing Irradiation for 393 Keloids, Borok, et al., Presentation 29th Annual Meeting of the American Soc. Thera. Radio. and Oncol., Boston, Mass., Oct. 1987.
Radiation Therapy Following Keloidectomy: A 20-Year Experience, Kovalic, et al. Int. J. Radiation Oncol. Biol. Phy., vol. 17, pp. 77–80; Jan. 18, 1989.
Technique of After-Loading Interstitial Implants, Syed, et al., Radiologia Clinica 46:458-475 (1977).
Temporary Iridium-192 Implant in the Management of Carcinoma of the Prostate, Puthawala, et al., Paper, dated Jan. 1985, Endoc. Hypertherm. Oncol., vol. 1.
Transperineal Interstitial-Intracavitary "Syed-Neblett" Applicator in the Treatment of Carcinoma of the Uterine Cervix, Syed, et al., Endocurie, Hypertherm. Oncol., vol. 2:1-13, 1986.

Primary Examiner—Kyle L. Howell
Assistant Examiner—J. Lacyk
Attorney, Agent, or Firm—Jeffrey G. Sheldon

[57] ABSTRACT

A method for preventing restenosis after angioplasty comprises internally radiating the treated portion of the lumen to prevent restenosis of the enlarged lumen portion. A device useful for radiating the treated portion comprises an elongated flexible catheter with radioactive means located in a distal section of the carrier. Stiffening elements are located along the length of the catheter to enable the catheter to be pushed through the tortuous segments of coronary or peripheral vasculature without crimping.

41 Claims, 2 Drawing Sheets

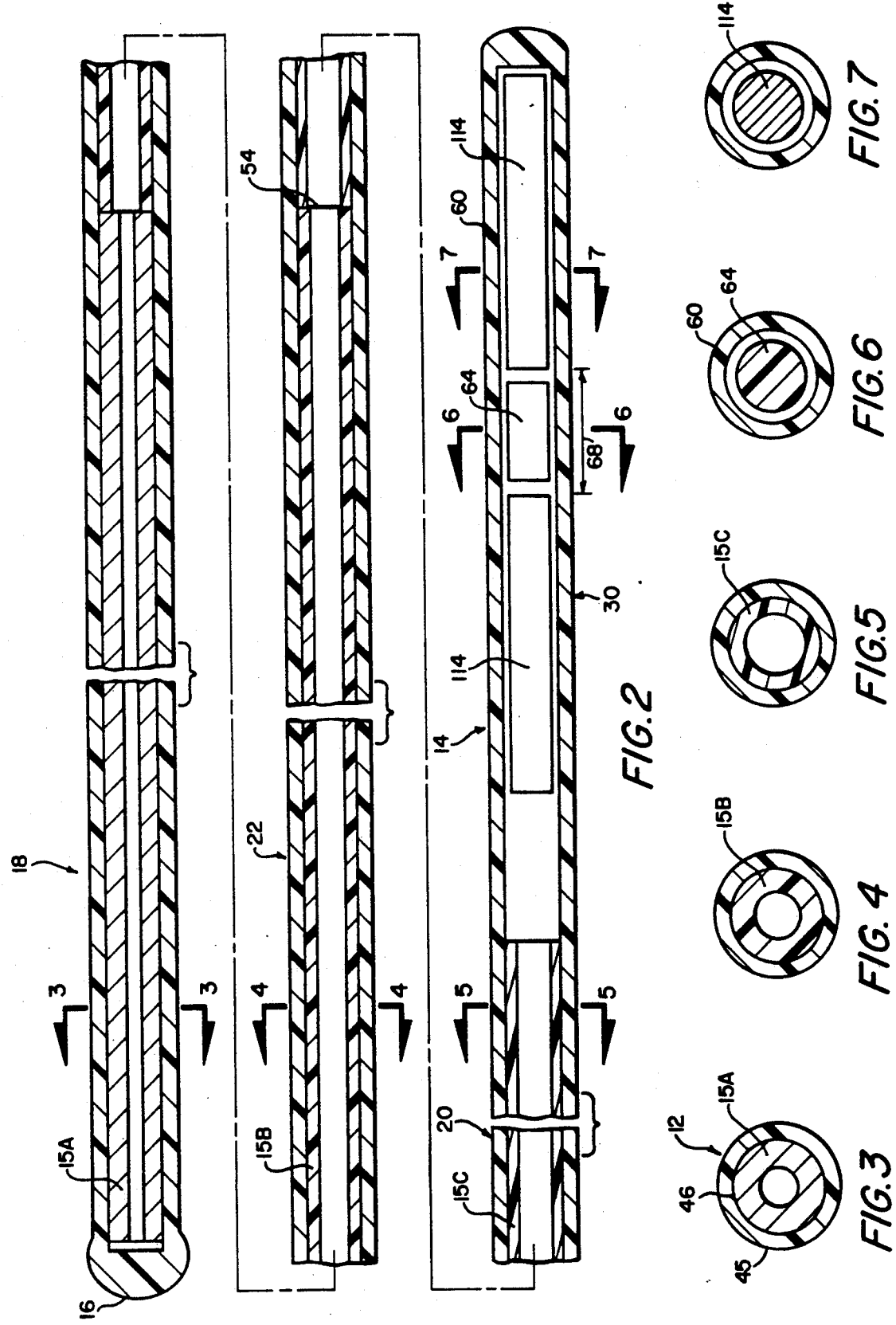

RADIOACTIVE CATHETER

BACKGROUND

This invention relates to a method for treating patients with obstructed arteries, and in particular, for preventing a renarrowing after standard therapies, an event which afflicts as many as 45,000 patients a year in the United States.

In 1964, a breakthrough in treating arterial disease occurred when a non-surgical technique to unblock vascular lumens became available. Known as percutaneous transluminal angioplasty (PTA), angioplasty today has become an accepted therapy for peripheral and coronary vascular disease, not only in the U.S., but internationally. The widespread use of PTA for the management of vascular disease is due to, among other factors, advances in percutaneous catheter technology and a high level of acceptance by patients of non-operative procedures.

The development of the balloon catheter in 1974 significantly contributed to the efficacy of PTA. In balloon angioplasty, a catheter equipped with a dilatable balloon is threaded intravascularly to the site of atherosclerotic narrowing of the vessel. Inflation of the balloon with concomitant compression of atheroma enlarges the atherosclerotic narrowing, and enlarges the lumen by stretching the vessel wall.

Complications can result from transluminal angioplasty. One serious complication is that of restenosis which frequently accompanies the various methods of angioplasty for treating coronary and non-coronary vasculature. Restenosis is the renarrowing of the vessel after angioplasty, and often requires multiple angioplastic procedures.

At present, there is no effective means for preventing restenosis following angioplasty, atherectomy or the newer modes of laser therapy for enlarging stenotic vessels.

In the United States, it is estimated that of the 300,000 patients yearly who undergo procedures involving angioplasty or atherectomy to remove stenotic lesions from coronary arteries, from 15% to 30% of those patients exhibit restenosis. Several studies document a restenosis rate of 25% to 35% within the first year following coronary angioplasty, with the vast majority of patients requiring repeat procedures within 6 months. Furthermore, the restenosis rate for angioplasty of the smaller, peripheral arteries also occurs at a significant rate.

Thus, a drawback of angioplasty is the frequent complication of restenosis, requiring a patient to undergo one or more repeat angioplastic procedures, which are costly and subject the patient to the risks associated with any medical procedure.

Another problem associated with angioplasty is crimping and puckering of the thin-walled, small diameter flexible catheters as they are pushed through twisting and turning sections of the vascular system. Similar to a thread being pushed through a tube, a thin-diameter, flexible catheter frequently crimps or kinks as it is being pushed through vascular lumen, delaying the procedure. Despite advances in catheter technology, the physician still faces the difficult and time-consuming task of manipulating the catheter when such crimping occurs.

Accordingly, there is a need for (a) a method to prevent the necessity for repeated lumen-enlarging procedures following angioplasty, and (b) a catheter that will not crimp or pucker when being pushed through twisting and turning sections of the vasculature system.

SUMMARY

The present invention meets these needs by providing a device or catheter that is suitable for treatment of a portion of a lumen in mammals and that avoids the crimping problem. A preferred version of the device is particularly suitable for preventing restenosis after coronary angioplasty. The invention also provides a method that inhibits restenosis after angioplasty.

The device comprises an elongated, flexible carrier having a proximal section, a distal section, and an intermediate section between the proximal and distal sections. At least two stiffening elements are immovably located along the length of the carrier so that the proximal section of the carrier is the stiffest section of the carrier and the distal section of the carrier is the most flexible section of the carrier. This allows the distal section to be advanced in transluminal movement to navigate tortuous turns in the lumen by pushing on the proximal section, without crimping the carrier. This differential stiffening of the carrier is achieved through the use of stiffening elements, rather than varying either the size or material of the carrier. Thus, the carrier has a substantially constant outer diameter, a substantially constant inner diameter, and is composed of a material whose composition does not vary along the length of the carrier.

Typically the device has three stiffening elements. The stiffest stiffening element is in the proximal section, the most flexible stiffening element is in the distal section, and a stiffening element having a stiffness intermediate that of the proximal and distal stiffening elements is in an intermediate section of the carrier, the intermediate section being between the distal and proximal sections.

The stiffening elements can be held immovably in the carrier by frictional engagement with the inner wall of the carrier. This can be accomplished by having the outer diameter of the stiffening elements about equal to or slightly larger than the inner diameter of the carrier.

A differentially stiffened catheter has many applications, including angioplasty. A preferred application of the device is endoluminal radiation treatment of a portion of a lumen to prevent stenosis and, in particular, restenosis in a lumen after angioplasty. In this application radioactive means are positioned in a radioactive portion of the distal section of the carrier, where the radioactive means are capable of providing in less than 30 minutes of exposure time sufficient radiation to the lumen to prevent restenosis after angioplasty. Restenosis can be avoided where the radioactive means provides about 3000 rads per hour along the length of the radioactive segment as measured at 3 mm from the longitudinal central axis of the carrier.

To prevent restenosis after angioplasty, the distal section is required to be sufficiently flexible to navigate the coronary artery of a human. For this reason, preferably the radioactive means comprises a plurality of cylindrically-shaped, radioactive pellets longitudinally spaced apart by spacers a sufficient distance to maintain the necessary flexibility. The length of the radioactive segment is about equal to the length of the lumen portion to be treated. In order to maintain the needed flexibility of the radioactive segment, the distal stiffening element terminates proximally to the position of the radioactive pellets.

So that the device can be fit into a coronary artery, preferably the carrier has an outer diameter of less than about 1 mm.

The device is used to avoid stenosis or restenosis by introducing the device so that the radioactive elements are in a selected section of the lumen, and then irradiating the selected section of the lumen with the radioactive elements for less than 30 minutes. After the lumen has been sufficiently radiated, the device is withdrawn from the lumen. This method is particularly suitable when the selected portion of the lumen has been enlarged with an endoluminal treatment device, such as by balloon dilation, cutting away obstructive lumenal lesions, or use of laser radiation. The device can be inserted into the lumen using an introducing catheter that has been properly positioned through use of a guide wire.

Accordingly, restenosis that frequently occurs after angioplasty can be avoided by irradiating the enlarged section of the coronary artery in a procedure that can be accomplished in less than 30 minutes. This is much better than having a patient undergo the expensive and time-consuming procedure of angioplasty with its attendant health risks.

DRAWINGS

These and other features, aspects, and advantages of the present invention will become better understood with reference to the following description, appended claims, and accompanying drawings where:

FIG. 2 is a longitudinal sectional view of the device of FIG. 1 taken on line 2—2 in FIG. 1;

FIGS. 3-5 are transverse cross-sectional views of the proximal, intermediate, and distal sections of the device of FIG. 1 taken on lines 3—3, 4—4, and 5—5 in FIG. 2, respectively;

FIG. 6 is a transverse cross-section in a space between radioactive beads in the radioactive segment of the distal section of the device of FIG. 1 taken on line 6—6 of FIG. 2;

FIG. 7 is a transverse cross-section of the radioactive segment of FIG. 2 through a radioactive bead;

Figure 1:
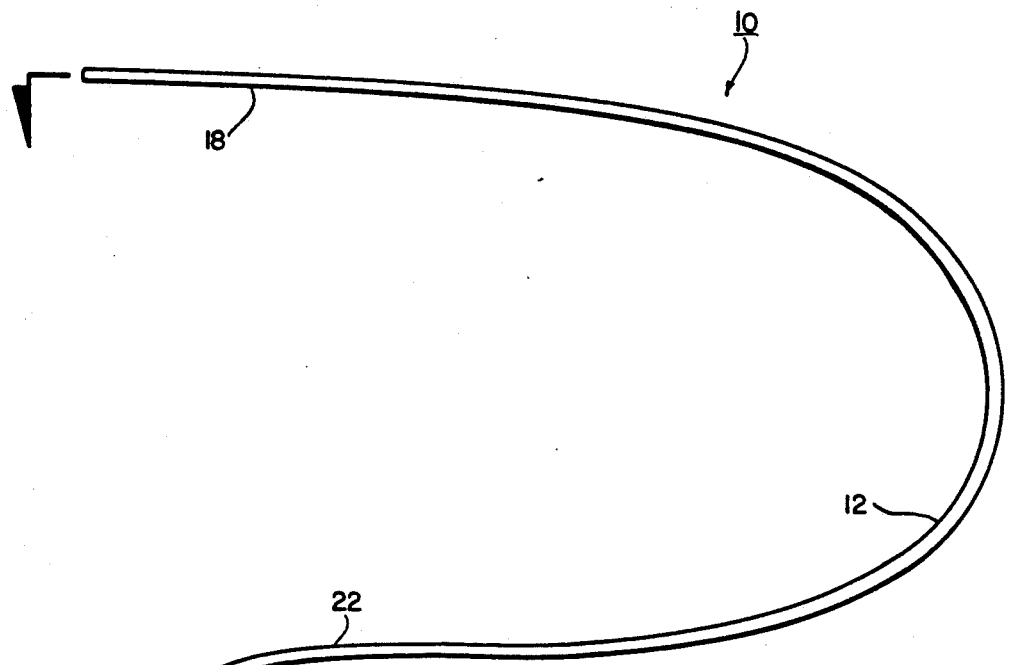
FIG. 1 is a top plan view of an irradiation device embodying features of the present invention.
Figure 8:
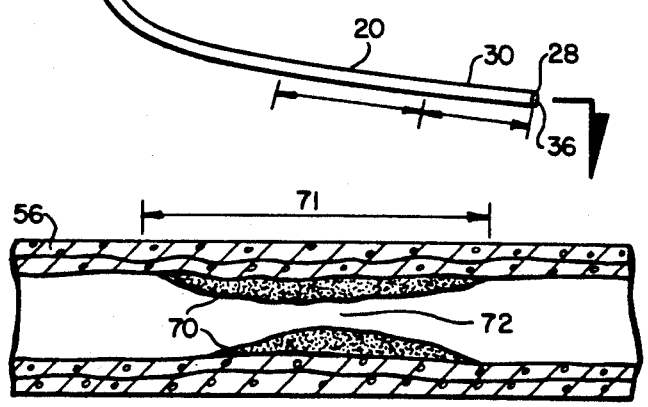
Figure 9:
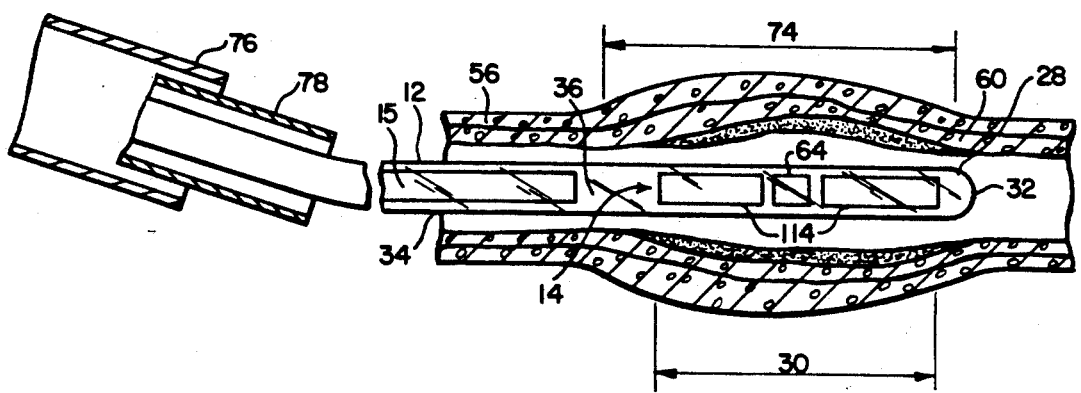

FIG. 8 is longitudinal sectional view of a segment of a narrowed, stenotic vascular lumen; and FIG. 9 is a longitudinal sectional view of a portion of vascular lumen immediately following a lumen-enlargement technique showing the radioactive segment of the distal section of the device in place proximate the enlarged portion of lumen, and schematically illustrating the deliverance of the device to the enlarged portion via a guide wire and an introducing catheter.

DESCRIPTION

The present invention is directed to (a) a method for preventing stenosis of a portion of a lumen in a human, (b) a method for enlarging a portion of a mammalian lumen and preventing stenosis of the enlarged portion, (c) an irradiating device for endoluminal radiation treatment of a portion of lumen which does not crimp when pushed through twisting and turning sections of the lumen, and (d) a device suitable for treatment of a portion of a lumen in mammals.

The method and device can be employed to prevent the recurrence of stenosis following enlargement of the lumen by a lumen-enlargement technique, e.g. angioplasty, in the peripheral vasculature and the coronary vasculature. By carrying and delivering radioactivity to the portion of enlarged endoluminal wall soon after the enlargement procedure, excessive growth of scar tissue from the endoluminal wall is inhibited. Therefore, risk that a patient will need to undergo repeated angioplastic interventions is reduced.

Because of the stiffening elements employed in the device, the device is capable of eliminating time-consuming manipulations required when crimping occurs in conventional devices pushed through tortuous segments of vasculature. The stiffening elements of the present invention differentially stiffen the length of the device, allowing it to be inserted and pushed through tortuous segments of vasculature without crimping.

With reference to the figures, an irradiating device 10 having features of the present invention comprises an elongated flexible, hollow catheter or carrier 12 (also referred to below as tube 12, radioactive means 14, and stiffening elements, namely a proximal stiffening element 15A, an intermediate 15B, and a distal stiffening element 15C.

The proximal section 18 extends from the proximal end 16 of the tube 12 to the end of the proximal stiffening element 15A. The proximal section 18 contains the proximal stiffening element 15A. The intermediate sections 22 extends from the distal end of the proximal section to the end of the intermediate stiffening element 15B. The intermediate section 22 is located between the proximal section 12 and the distal section 20. The distal section 20 of the tube 12 extends from the distal end of the intermediate section 20 to the distal end 28 and includes a closed distal end 28. A radioactive segment 30 is located in the distal section 20. Within the radioactive segment 30 are located the radioactive means 14. The carrier 12 has a substantially constant outer diameter and is comprised of a homogenous material.

The carrier can be a plastic, such as a fluoropolymer or can be a metal, such as stainless spring steel. A preferred material for the tube is a radiation resistant fluoropolymer, such as Tefzel TM fluoropolymer.

The outer diameter of the carrier 12 is sufficiently small that it can be inserted within a lumen 34. Preferably the outer diameter is less than about 1 mm for insertion into a human vascular lumen within the heart. The length of the tube 12 varies depending on the portion of lumen 34 selected for treatment. The carrier 12 typically has a length of from about 90 cm to about 150 cm. In transverse cross-section, the axial passage 36 of the tube 12 can be circular. The wall thickness of the tube is substantially constant along the length of the tube 12.

The stiffening elements 15 are located within the tube 12, extending from the proximal end one after the other, i.e. serially, along the axial passage 36 of the tube 12. By matching the outer diameters of the stiffening elements 15 to the inner diameters of the tube 12, the stiffening elements 15 are immovably placed within the tube 12 by means of frictional engagement between the outer circumferential surface 45 of the stiffening element 15 and the inner wall surface 46 of the tube 12.

The stiffening elements 15 can be made of metal or plastic fluoropolymers. The stiffening elements 15 are selected so that the proximal section 18 of the tube 12 is the stiffest section of the tube 12. A preferred material for the stiffening element 15A in the proximal section 18 is a seamless, stainless steel tubing, with an outer diameter of 0.55 mm and inner diameter of 0.010 inches. The intermediate stiffening element 15B is selected so that it is intermediate in stiffness between the proximal 15A and distal 15C stiffening elements. A preferred material for the intermediate stiffening element 15B is regular Teflon ™ tubing grade TFE-tetrafluoroethylene. The distal stiffening element 15C is the most flexible stiffening element:. In a preferred arrangement, the distal stiffening element 15C is a section of tube made of the same material as the flexible, elongated tube 26. Accordingly, a preferred material for the distal stiffening element 15C is Tefzel ™ grade ETFE-ethylene tetrafluoroethylene.

The distal stiffening element 15C extends only partially from the distal end 54 of the intermediate stiffening element 15B to the radioactive segment 30 in the distal section 20, terminating proximally to the radioactive segment 30.

The radioactive means 14 can be any nuclide. A preferred material is iridium 192. The radioactive means can be any shape and can be placed onto or into a carrier 12, or manufactured into the material of the carrier 12. A preferred radioactive means is a plurality of cylindrical, radioactive pellets 14 having a sufficiently small diameter to fit within the tube. The pellets 14 can be held in place by short spacers 64 between successive pellets. The spacers 64 can be cylindrically shaped with diameters equal to the inner diameter of the tube 12. Thus, the spacer lengths 64 frictionally engage the inner wall surface 46 of the tube 12. Spacer length can be the same plastic material as the tube. The radioactive means 14 can thus be spaced apart from each other and arranged longitudinally. The spacing is sufficiently far apart that the radioactive segment 30 of the tube 12 is sufficiently flexible that the distal section 20 can navigate tortuous, twisting sections of lumen by pushing on the proximal section 18 without crimping the tube 12. A typical space 68 between radioactive beads 63 is 1 mm.

While a preferred configuration of the radioactive means is spaced-apart, cylindrically-shaped pellets, any solid shape of the radioactive means which would maintain the necessary flexibility of the distal section would be of satisfactory utility. The radioactive means can also include liquids, gases, or powders by themselves or in any combination with each other or in combination with a solid radioactive means. As a liquid, gas, or powder, the radioactive means can be either fixed in place in the distal section before the distal section is placed in a lumen; or once the distal section is in place in a lumen, the radioactive means can be injected into the distal section.

It is believed that in order to prevent restenosis, it is necessary to deliver to the tissue from about 25 to about 2500 rads per centimeter length of lumen treated, and preferably from about 100 to about 1000, and most preferably about 250 per centimeter length of lumen treated. It is desired that this be accomplished in less than 30 minutes to minimize the amount of time the patient is subject to the procedure. Preferably, the procedure takes less than about 25 minutes. More preferably less than about 15 minutes, but typically it requires at least about 10 minutes.

To deliver this amount of radiation in this time, it is necessary that the total radiation provided by the radiation means be from about 100 to about 10,000, preferably from about 500 to about 5,000, and typically about 3000 rads per hour along the length of the radio-active segment as measured at 3 mm from the longitudinal central axis of the carrier 12. This result can be effected by providing sufficient radioactive pellets 114 that the radioactive means 14 provides from 0.01 to about 100,000 millicuries, and preferably from about 50 to 500, and typically about 100 millicuries per centimeter length of radioactive segment.

The device 10 is easily used to prevent restenosis of a segment of a lumen 34 in a human. After a selected portion 71 of the lumen 34 is enlarged with an endoluminal treatment device, the enlarged portion 71 is irradiated with the radioactive means 14. The lumen 34 can be enlarged by dilating the lumen 34 by inflating a balloon inside the lumen 34, by cutting away obstructive luminal lesions 70, or by irradiating a narrowed section 72 of the lumen 34 with laser radiation.

The device 10 is inserted into the selected portion 71 of the lumen 34 so that the radioactive means 14 is proximate to the enlarged portion 74 of the lumen 34, and left in the lumen 34 for a sufficiently long time that a sufficient amount of radioactivity is delivered to the enlarged portion 74 to prevent stenosis.

The above method is typically used in combination with devices that facilitate placement of a coronary balloon dilation catheter during angioplasty. These facilitating device can be a guide wire 76 and an introducing catheter 78. Before the radioactive device 10 is placed in a lumen 34, a guide wire 76 can first be inserted into a length of vasculature. An introducing catheter 78 is then inserted into the guide wire 76. The selected radioactive device 10 is then inserted into the probing catheter 78 so that the distal section 20 of the device 10 extends beyond the end of the probing catheter 78 such that the radioactive segment 30 is placed proximate to the selected portion 71 of enlarged lumen 34.

The method for preventing restenosis has applications other than preventing restenosis after an angioplastic procedure. For example, the material and device 10 can be used to prevent restenosis after traumatic injury to a lumen, or after other repair procedure on a lumen where scar formation ensures.

The method and device of the present invention are advantageous because they overcome the problem of restenosis associated with conventional angioplasty and other methods of moving atherosclerotic plaques from arterial walls. By reducing the incidence of restenosis, the necessity for a patient to undergo another angioplastic procedure is eliminated, with considerable savings to the patient of money and risk. The differential stiffening aspect of the device that prevents crimping is advantageous because it simplifies the task of threading an extremely flexible carrier through tortuous, twisting sections of lumens, thus saving time and shortening the length of the procedure.

EXAMPLES

In this example, a device according to the present invention was constructed and tested for reliability and safety of delivering the device to targeted portions of coronary vasculature in dogs.

In each of 12 dogs, the device (as described below) was delivered to three portions of coronary vasculature: (1) a control portion, which was neither injured by balloon angioplasty nor irradiated endoluminally; (2) an experimental portion, which was irradiated by the device; and (3) an experimental portion which was treated by balloon angioplasty and irradiated endoluminally by means of the device.

The device, either with or without radioactive means, was left in place for 30 minutes to 45 minutes. With radioactive means in place, 500 rads of radiation were delivered to the selected portion of vascular lumen. Within three days, the coronary portions were examined microscopically.

The results indicate that the device did not interrupt blood flow or cause functional abnormalities. Acute problems were not demonstrable in the control portions nor in the experimental portions beyond the effects of the balloon angioplasty itself. Placement of the device and delivery of radiation under this protocol did not appear to cause short-term, acute injury in the selected portions of coronary vasculature.

In this example, the device was constructed for endoluminal radiation treatment of a portion of canine coronary vasculature. The device comprised a hollow elongated tube made of lightweight wall radiation-resistant Tefzel TM tubing (grade ETFE-ethylene tetrafluoroethylene).

The outer diameter of the tube was 0.88 mm and the inner diameter was 0.55 mm. The distal end of the device was closed. Six radioactive pellets were serially arranged over a 2 cm length—the radioactive segment—near the distal end. The most distal pellet was placed in contact with the closed distal end. The outer diameter of the radioactive pellets was 0.50 mm. Each pellet was 3 mm in length. The pellets were held in place and spaced apart by placement of 1 mm spacer lengths of Tefzel TM tubing having an outer diameter of 0.55 mm, equal to the inner diameter of the hollow, elongated tube. The outer wall of the 1 mm spacer lengths of Tefzel TM were in frictional contact with the inner wall of the elongated Tefzel tubing of the device. Each pellet provided 34 millicuries, for a total radioactivity of 204 millicuries. The pellets were made of radioactive iridium 192.

Three stiffening elements were placed in the hollow, elongated Tefzel TM tubing to provide differential stiffness that would permit the distal section of the device to navigate luminal tortuosities without the device crimping. Each stiffening element had an outer diameter of 0.55 mm, which placed it in frictional engagement with the inner wall of the hollow, elongated Tefzel TM tubing. The proximal stiffening element was about 45 cm long and was made of flexible, seamless, stainless steel tubing, 25 gauge fullhard. The intermediate stiffening element was a 78 cm-length of regular Teflon TM rod tubing, grade TFE, less stiff than the stainless steel tubing. The most distal stiffening element was a 10 cm-length of Tefzel TM tubing, which terminated 2 mm before the position of the radioactive pellets. A 1 mm length of 0.55 mm outer diameter Tefzel TM was placed between the termination of the distal stiffening element and the first radioactive pellet.

Although the present invention has been described in considerable detail with regard to certain preferred versions, other versions are possible. For example, non-radioactive as well as radioactive versions can be constructed. Instead of radioactive means placed in a distal section, a lumen enlarging mechanism can be located in the distal section 20. The lumen enlarging mechanism can be an angioplasty balloon, an atherectomy device, an endovascular stent, or a source of laser radiation. Use can be made of differential stiffening in the proximal 18, intermediate 22 and distal 20 sections.

Only two stiffening elements or more than three stiffening elements can be used. The number of stiffening elements and the relative lengths required of each for a particular application can depend on the lumen selected for treatment and its location in the body. Elongated stiffening elements can be employed with variable instead of constant stiffness along their lengths. The stiffening elements can be immovably fitted within the tube by means other than friction fitting. For example, the stiffening elements can be glued in. Furthermore, it should be understood that stiffening elements can be arranged in parallel or in partial parallel, i.e., overlapping arrangements.

Although the present invention has been described in considerable detail with reference to certain preferred versions thereof, other versions are possible. For example, the stiffening feature need not be limited to a catheter having radioactive elements. For example, the catheter may have an endovascular stent coaxially mounted on the distal section. Another alternative is a catheter with stiffening elements, including a radioactive distal section with an angioplasty balloon such that angioplasty and radiation treatment can be accomplished at the same time. Similarly, the radiation treatment to avoid stenosis is not limited to applications immediately after angioplasty. Further, the method and device can be employed for preventing restenosis in other lumens beside the vasculature. The method and device have utility in the restoration and maintenance of patency to previously narrowed or otherwise defective or impaired lumens or other body channels. Such body channels may include the esophagus, bile ducts, urethra, trachea, and the like.

Other specific uses for the methods and devices embodying features of the present invention include the repair or correction of intraluminal lining of AAA or iliac or femoral aneurysms; recanalization of injured vessels caused by blunt or penetrating trauma; recanalization of esophageal stenoses secondary to carcinoma or benign structures; dilation and recanalization of coarctation of aorta; dilation and recanalization of biliary stenoses secondary to strictures, tumors and cancer of pancreas and common bile duct; and ureteral strictures and tracheal strictures.

It should be understood that the above list is not intended to be exclusive and that any body vessel which has been narrowed, weakened, or in another way requires a repair or reinforcement may be subject to the present invention. Also, as used herein, the term lumen is used in generic sense to include body channels including, but not limited to, artery, esophagus, bile duct, urethra, trachea, and the like and the term body includes not only human but animals as well.

However, in view of the high dosages of radiation provided by the device 10, it is clearly not suitable for long term implantation in a human as is typically done with cancer treatment.

Accordingly, the spirit and scope of the appended claims should not be limited to the description of the preferred versions contained herein.

What is claimed is:

1. A device suitable for endoluminal radiation treatment of a portion of a coronary artery in humans, the device comprising:
   (a) an elongated, flexible carrier having a proximal section and a distal section; and
   (b) radioactive means positioned in a radioactive segment of the distal section of the carrier, the radioactive means providing radiation in an amount from 0.01 to 100,000 millicuries per centimeter length of the radioactive portion, wherein the carrier is sized and has sufficient stiffness and flexibility to navigate a human coronary artery so that the radioactive segment can be placed in a selected portion of a human coronary artery, the radioactive means when so placed providing sufficient radiation in less than 30 minutes to prevent restenosis in the selected portion after angioplasty.

2. The device of claim 1 wherein the radioactive means provides from about 50 to about 500 millicuries per centimeter length of the radioactive portion.

3. The device of claim 1 wherein the radioactive means provides from about 100 to about 10,000 rads per hour measured at 3 millimeters from the longitudinal central axis of the carrier.

4. The device of claim 3 wherein the radioactive means provides from about 500 to about 5000 rads per hour measured at 3 millimeter from the longitudinal central axis of the carrier.

5. The device suitable for treatment of a portion of a lumen in mammals, the device comprising:
 (a) an elongated, flexible carrier having a proximal section, an intermediate section, and a distal section; and
 (b) at least three separate stiffening elements immovably located along the length of the carrier so that the proximal section of the carrier is the stiffest section of the carrier and the distal section of the carrier is the most flexible section of the carrier so that the intermediate section of the carrier has a stiffness intermediate the stiffness of the proximal section and the stiffness of the distal section, so that the distal section can be advanced in transluminal movement to navigate tortuous turns in the lumen by pushing on the proximal section without crimping the carrier; and
 (c) radioactive means positioned in a radioactive segment of the distal section of the carrier, the radioactive means providing radiation in an amount from 0.01 to 100,000 millicuries per centimeter length of the radioactive segment, wherein the carrier is sized and has sufficient stiffness and flexibility to navigate a human coronary artery so that the radioactive portion can be placed in a selected portion of a human coronary artery, the radioactive means when so placed providing sufficient radiation in less than 30 minutes to prevent restenosis in the selected portion after angioplasty.

6. The device of claim 1 or 5 wherein the radioactive means provides from about 100 to about 1000 rads per hour along the length of the radioactive segment measured at 3 mm from the longitudinal axis of the carrier.

7. The device of claim 5 wherein the carrier has a substantially constant outer diameter, a substantially constant inner diameter, and is composed of a material whose composition does not vary along the length of the carrier.

8. The device of claim 1 or 5 wherein the length of the radioactive segment is about equal to the length of the portion of the coronary artery to be treated.

9. The device of claim 5 including an introducing catheter through which the carrier is pushed, the inner diameter of the introducing catheter being larger than the outer diameter of the carrier and the length of the carrier being greater than the length of the introducing catheter.

10. The device of claim 5 wherein the radioactive means comprises a plurality of radioactive beads in the radioactive segment of the carrier, the beads being sufficiently spaced apart from each other that the radioactive segment is sufficiently flexible to navigate tortuous turns in the lumen by pushing on the proximal section without crimping of the carrier, the stiffening element in the distal section of the carrier not extending into the radioactive segment.

11. A device suitable for endoluminal radiation treatment of a portion of lumen in a mammal, the device comprising:
 (a) a hollow, elongated flexible tube having an axial passage, the tube having a proximal section, a distal section, and an intermediate section between the proximal and distal sections, the distal section including a distal end, the tube having a substantially constant outer diameter, a substantially constant inner diameter, and being composed of a material whose composition does not vary along the length of the carrier;
 (b) radioactive means positioned in a radioactive segment of the distal section of the tube proximate to the distal end, the radioactive means providing sufficient radiation, in an amount from 0.01 to 100,000 millicuries per centimeter length of the radioactive segment, that when the radioactive portion is placed in the portion of the lumen for an exposure time less than 30 minutes, restenosis in the portion of the lumen is prevents; and
 (c) at least three separate stiffening elements immovably and serially located within the tube and extending longitudinally along the axial passage of the tube for differentially stiffening the proximal, intermediate, and distal sections of the tube, the stiffening elements being selected so that the proximal section of the tube is the stiffest section of the tube, the distal section of the tube is the most flexible section of the tube, and the intermediate section of the tube has a stiffness intermediate the stiffness of the proximal section and the stiffness of the distal section so that the distal section can be advanced in transluminal movement to navigate tortuous turns in the lumen by pushing on the proximal section without crimping the tube.

12. The device of claim 11 wherein the stiffening element in the distal section is a hollow tube stiffener element formed of the same material as the hollow tube.

13. The device of claim 11 wherein the axial passage of the tube is circular in cross-section and the stiffening elements are circular in transverse cross section and have a sufficiently large outer diameter that they are in frictional engagement with the inner wall of the tube.

14. The device of claim 11 wherein each stiffening element has substantially the same flexibility along its length.

15. The device of claim 11 wherein the radioactive means comprises a plurality of radioactive beads in the radioactive segment of the tube, the beads being sufficiently spaced apart from each other that the radioactive segment is sufficiently flexible to navigate tortuous turns in the lumen by pushing on the proximal section without crimping of the tube, the stiffening element in the distal section of the tube not extending into the radioactive segment.

16. The device of claim 7, 11, or 13 wherein each stiffening element has a substantially constant wall thickness.

17. A device for endoluminal radiation treatment of a portion of a lumen in human beings, the device comprising:
  (a) a hollow elongated flexible tube of outer diameter of less than about 1 mm, the tube having a proximal section, a distal section and an intermediate section between the proximal and distal sections, the distal section including a distal end;
  (b) a plurality of radioactive beads positioned in a radioactive segment within the distal section of the tube proximate to the distal end of the tube, the radioactive beads providing sufficient radiation in an amount from 0.01 to 100,000 millicuries per centimeter length of the radioactive segment, that when the radioactive segment is placed in a selected portion of a human lumen for less than 30 minutes, restenosis in the selected portion of lumen is prevented;
  (c) at least three separate stiffening elements immovably and serially located within the tube and extending longitudinally along the axial passage of the tube for differentially stiffening sections of the tube, the stiffening elements comprising a proximal stiffening element in a proximal section of the tube, a distal stiffening element in a distal section of the tube, and an intermediate stiffening element in an intermediate section of the tube between the distal and proximal sections, wherein the proximal stiffening element is the stiffest stiffening element, the distal stiffening element is the least stiff stiffening element, and the intermediate stiffening element has a stiffness intermediate the stiffness of the proximal and distal stiffening elements;
  (d) means for maintaining radioactive beads spaced apart from each other so that the radioactive segment of the tube is flexible; and
  wherein the distal stiffening element is sufficiently flexible and the beads are sufficiently spaced apart from each other that the distal section can be advanced in transluminal movement to navigate tortuous turns in the lumen by pushing on the proximal section without crimping the tube and that the radioactive segment of the tube can navigate tortuous turns in the lumen.

18. The device of claim 11 or 17 wherein the length of the tube is at least about 90 cm, and wherein the length of the proximal stiffening element is from about 30 cm to about 60 cm, the length of the intermediate stiffening element is from about 65 cm to about 90 cm, and the length of the distal stiffening element is from about 5 cm to about 15 cm.

19. The device of claim 11 or 17 wherein the radioactive beads are spaced part by about 1 mm.

20. The device of claim 17 wherein the total activity of the radioactive beads is about 50 to about 500 millicuries per centimeter of length of the radioactive segment.

21. The device of claim 17 wherein the length of the radioactive segment is about 2 centimeters.

22. The device of claim 11 or 17 wherein the length of the distal stiffening element in the distal section of the tube terminates proximally to the position of the radioactive beads.

23. The device of claim 11 or 17 wherein the distal section is sufficiently flexible that the radioactive segment can enter the human coronary artery.

24. A method for preventing stenosis of a selected portion of a lumen in a mammal comprising the steps of:
  (a) introducing a flexible, elongated carrier having a radioactive segment carrying radioactive elements into the lumen so that the radioactive elements are in the selected section of the lumen;
  (b) irradiating the selected section of lumen with the radioactive elements for no more than about 45 minutes, the amount of radiation delivered to the selected section of lumen being at least about 25 rads per cm length of the selected section of the lumen; and
  (c) withdrawing the carrier.

25. The method of claim 24 wherein at least about 100 rads per cm length of the selected section of the lumen are delivered.

26. The method of claim 24 or 25 wherein the step of irradiating comprises delivering up to about 1000 rads per centimeter length of the radioactive segment.

27. The method of claim 24 wherein the amount of radiation delivered is up to about 2500 rads per centimeter length of the selected section of the lumen.

28. The method of claim 24 wherein the step of irradiating comprises irradiating the selected section for no more than 30 minutes.

29. A method for enlarging the luminal cross-section of a selected portion of a mammalian lumen and preventing stenosis of the enlarged portion, the method comprising the steps of:
  (a) enlarging the selected portion of the lumen with an endoluminal treatment apparatus having an outer diameter sufficiently small that the apparatus fits in the lumen;
  (b) inserting a device having a radioactive segment comprising radioactive means into the enlarged portion of the lumen so that the radioactive means is proximate to the enlarged portion of the lumen;
  (c) leaving the device in the lumen with the radioactive means proximate to the enlarged portion of the lumen for internally radiating the enlarged portion of the lumen with sufficient radioactivity in an amount from about 25 to about 2500 rads per centimeter length of the radioactive segment to prevent stenosis of the enlarged lumen portion; and
  (d) thereafter withdrawing the device from the lumen.

30. The method of claim 29 wherein the step of leaving the device in the lumen comprises radiation the enlarged portion for less than about 30 minutes.

31. The method of claim 31 wherein the lumen comprises a section of the vasculature of a human.

32. The method of claim 29 wherein the section of vasculature is a coronary artery.

33. The method of claim 29 wherein the step of enlarging the selected portion of the lumen comprises dilating the lumen using a balloon inside the lumen.

34. The method of claim 29 wherein the device comprises:
  an elongated, flexible carrier having a proximal section and a distal section; and
  wherein the radioactive means is positioned in a radioactive segment of the distal section of the carrier, the radioactive means providing from about 0.01 to 100,000 millicuries per centimeter length of the radioactive segments.

35. The method of claim 29 wherein the device provides from about 100 to about 1000 rads per hour per centimeter length of radioactive segment measured at 3 mm from the outer circumferential surface of the device.

36. The method of claim 29 wherein the device comprises:
   (a) an elongated, flexible carrier having a proximal section, a distal section and an intermediate section between the proximal and distal sections; and wherein the radioactive means is positioned in a radioactive segment of the distal section of the carrier; and
   (b) at least three separate stiffening elements immovably located along the length of the carrier for differentially stiffening the proximal, intermediate, and distal sections of the carrier, the stiffening elements being selected so that the proximal section of the carrier is the stiffest section of the carrier, the distal section of the carrier is the most flexible section of the carrier, and the intermediate section of the carrier has a stiffness intermediate the stiffness of the proximal section and the stiffness of the distal section so that the distal section can be advanced in transluminal movement to navigate tortuous turns in the lumen by pushing on the proximal section without crimping the carrier.

37. The method of claim 29 wherein the step of inserting the device in the lumen comprises the steps of:
   (a) inserting a guide wire into the lumen;
   (b) inserting a probing catheter into the guide wire; and
   (c) inserting the device into the introducing catheter so that the distal section of the device extends beyond the distal end of the introducing catheter such that the radioactive segment is placed proximate to the enlarged portion of the lumen.

38. The method of claim 29 wherein the step of inserting the device into the lumen is accomplished from about 1 minute to about 10 minutes after the step of enlarging the selected portion of the lumen.

39. The method of claim 29 wherein the step of leaving the device in the lumen comprises leaving the device in the lumen a sufficient time to deliver from about 100 to about 1000 rads per centimeter length of the enlarged lumen.

40. The device of claim 1 or 5 wherein the carrier has an outer diameter of less than about 1 mm.

41. The device of claim 40 wherein the length of the carrier is at least about 90 cm.

* * * * *

REEXAMINATION CERTIFICATE (3606th)

United States Patent [19]
Dake et al.

[11] B1 5,199,939
[45] Certificate Issued Aug. 18, 1998

[54] RADIOACTIVE CATHETER

[76] Inventors: Michael D. Dake, 1915 Mandeville Canyon Rd., Los Angeles, Calif. 90049; Bruce Hedger, 16220 Gundry Ave., Paramount, Calif. 90723; Stephen Oesterle, 101 Burlingame Ave., Los Angeles, Calif. 90049

Reexamination Requests:
No. 90/003,914, Oct. 10, 1995
No. 90/004,313, Jul. 25, 1996

Reexamination Certificate for:
Patent No.: 5,199,939
Issued: Apr. 6, 1993
Appl. No.: 484,117
Filed: Feb. 23, 1990

[51] Int. Cl.$^6$ .................................... A61N 5/00
[52] U.S. Cl. .................................... 600/3; 600/8; 600/436
[58] Field of Search .................... 600/1–18, 433–436; 128/656–659

[56] References Cited

U.S. PATENT DOCUMENTS 5,084,002  1/1992  Liprie .......................................... 600/7

OTHER PUBLICATIONS

M. Friedman, *Pathogenesis of Spontaneous Atherosclerotic Plaque*, Archives of Pathology, vol. 75, pp. 318–329 (Sep. 1963).

M. Friedman, et al., *Cortisone and Experimental Atherosclerosis*, Archives of Pathology, vol. 77, pp. 142–158 (Feb. 1964).

M. Friedman, et al., *The Antiatherogenic Effect of Iridium$^{192}$ upon the Cholesterol-fed Rabbit*, Journal of Clinical Investigation, vol. 43, No. 2 (1964).

M. Friedman, et al., *Aortic Atherosclerosis Intensification in Rabbits by Prior Endothelial Denudation*, Archives of Pathology, vol. 79, pp. 345–356 (Sep. 1965).

M. Friedman, et al., *Effect of Iridium 192 Radiation on Thromboatherosclerotic Plaque in the Rabbit Aorta*, Archives of Pathology, vol. 80, pp. 285–290 (Sep. 1965).

S. King, III, J. Douglas, et al., *Percutaneous Transluminal Coronary Angioplasty* in *Coronary Arteriography and Angioplasty*, pp. 433–460 (1985).

D. Faxon, et al., *Mechanism of Angioplasty and Its Relation to Restenosis*, The American Journal of Cardiology, vol. 60, pp. 114–118 (Jul. 31, 1987).

T. Borok, et al., *Role of Ionizing Irradiation For 393 Keloids*, International Journal of Radiation Oncology, Biology and Physics, vol. 15, Nov. 4, pp. 865–870 (Oct. 1988).

J. Kovalic, et al., *Radiation Therapy Following Keloidectomy: A 20-Year Experience*, International Journal of Radiation Oncology, Biology and Physics, vol. 17, No. 1, pp. 77–80 (Jul., 1989).

Z. Weshler, et al., Abstract, *Prevention of Neointimal Formation in De-endothilialized Rat Aorta*, European Society of Radiation Biology, 21st Annual Meeting (Tel Aviv, Israel; Oct. 1988).

Z. Weshler, et al., *Inhibition by Irradiation of Smooth Muscle Cell Proliferation in the De-endothilialized Rat Aorta*, Proceedings of 21st Annual Meeting of European Society of Radiation Biology, pp. 133–138 (1990).

H.D. Bottcher, et al., *Endovascular Irradiation—A New Method to Avoid Recurrent Stenosis After Stent Implantation in Peripheral Arteries: Technique and Preliminary Results*, International Journal of Radiation, Oncology, Biology and Physics, vol. 29, No. 1 pp. 183–186 (1994).

*Primary Examiner*—Lee S. Cohen

[57] ABSTRACT

A method for preventing restenosis after angioplasty comprises internally radiating the treated portion of the lumen to prevent restenosis of the enlarged lumen portion. A device useful for radiating the treated portion comprises an elongated flexible catheter with radioactive means located in a distal section of the carrier. Stiffening elements are located along the length of the catheter to enable the catheter to be pushed through the tortuous segments of coronary or peripheral vasculature without crimping.

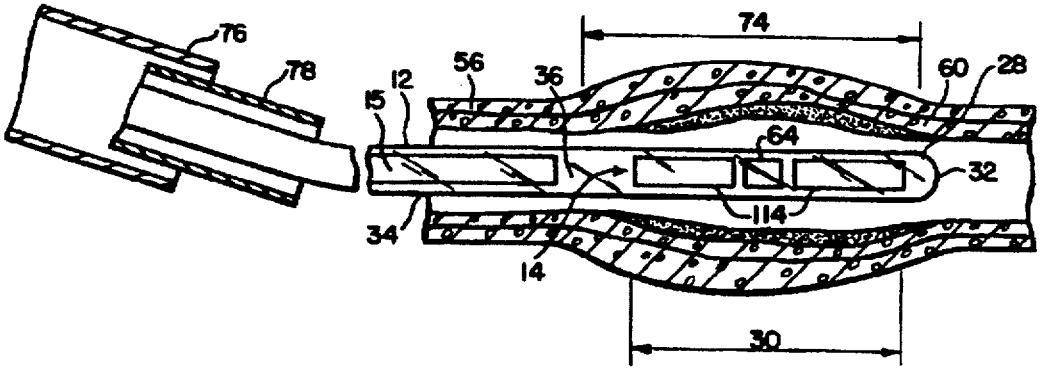

1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, Lines 51–61:

It is believed that in order to prevent restenosis, it is necessary to deliver to the tissue from about 25 to about 2500 rads [per centimeter length] *along the length* of lumen treated, and preferably from about 100 to about 1000, and most preferably about 250 [per centimeter length] *along the length* of lumen treated. It is desired that this be accomplished in less than 30 minutes to minimize the amount of time the patient is subject to the procedure. Preferably, the procedure takes less than about 25 minutes. More preferably less than about 15 minutes, but typically it requires at least about 10 minutes.

Column 5, line 62 to Column 6 line 5:

To delivery this amount of radiation in this time, it is necessary that the total radiation provided by the radiation means be from about 100 to about 10,000, preferably from about 500 to about 5,000, and typically about 3000 rads per hour along the length of the [radio-active] *radioactive* segment as measured at 3 mm from the longitudinal central axis of the carrier 12. This result can be effected by providing sufficient radioactive pellets 114 that the radioactive means 14 provides from 0.01 to about 100,000 millicuries, and preferably from about 50 to 500, and typically about 100 millicuries per centimeter length of radioactive segment.

AS A RESULT OF REEXAMINATION, IT HAS BEEN DETERMINED THAT:

Claims 1–6, 11, 14, 15, 17, 19, 20, 22–25, 27, 29–32, 34, 35, and 39 are determined to be patentable as amended.

Claims 7–10, 12, 13, 16, 18, 21, 26, 28, 33, 36, 37, 38, 40 and 41, dependent on an amended claim, are determined to be patentable.

New claims 42–65 are added and determined to be patentable.

1. A device suitable for endoluminal radiation treatment of a portion of a coronary artery in humans *after angioplasty*, the device comprising:

(a) an elongated, flexible carrier having a proximal section and a distal section; and (b) radioactive means positioned in a radioactive segment of the distal section of the carrier, the radioactive means providing radiation in an amount *selected within a range* from 0.01 to 100,000 millicuries per centimeter length of the radioactive [portion] *segment, wherein the carrier is sized and has sufficient stiffness and flexibility to navigate a vascular system to the* human coronary artery so that the radioactive segment can be placed in a selected portion of [a] *the* human coronary artery,

2

[the] *and wherein the device has sufficient* radioactive means [when] *that when the radioactive segment is* so placed [providing] *the radioactive means provides* sufficient radiation in less than 30 minutes to prevent restenosis in the selected portion *of the coronary artery after subjection thereof to* angioplasty.

2. The device of claim 1 wherein the radioactive means provides *radiation of a selected amount in a range* from about 50 to about 500 millicuries per centimeter length of the radioactive [portion] *segment*.

3. The device of claim 1 wherein the radioactive means provides *radiation of a selected amount within a rate range* from about 100 to about 10,000 rads per hour measured at *a distance of* 3 millimeters from the longitudinal central axis of the carrier.

4. The device of claim 3 wherein the radioactive means provides *radiation of a selected amount within a rate range* from about 500 to about 5000 rads per hour measured at *a distance of* 3 [millimeter] *millimeters* from the longitudinal central axis of the carrier.

5. [The] *A* device [suitable] for treatment of a portion of a lumen *of a coronary artery* in mammals *after angioplasty*, the device comprising:

(a) an elongated, flexible carrier having a proximal section, an intermediate section, and a distal section; and (b) at least three separate stiffening elements immovably located along the length of the carrier [so] *such* that the proximal section of the carrier is the stiffest section of the carrier, and the distal section of the carrier is the most flexible section of the carrier [so that], *and* the intermediate section of the carrier has a stiffness intermediate the stiffness of the proximal section and the stiffness of the distal section, [so] *such* that the distal section can be advanced in transluminal movement to navigate tortuous turns in the lumen by pushing on the proximal section without crimping the carrier; and (c) radioactive means positioned in a radioactive segment of the distal section of the carrier, the radioactive means providing radiation in an amount *selected within a range* from 0.01 to 100,000 millicuries per centimeter length of the radioactive segment, wherein the carrier is sized and has sufficient stiffness and flexibility to navigate a human coronary artery so that the radioactive [portion] *segment* can be placed in a selected portion of a human coronary artery, the radioactive means when so placed providing sufficient radiation in less than 30 minutes to prevent restenosis in the selected portion *of the coronary artery* after angioplasty.

6. The device of claim 1 or 5 wherein the radioactive means provides *radiation in an amount within a rate range* from about 100 to about 1000 rads per hour along the length of the radioactive segment measured at *a distance of* 3 mm from the longitudinal axis of the carrier.

11. A device suitable for endoluminal radiation treatment of a portion of [lumen] *an artery* in a mammal *which has been subjected to angioplasty*, the device comprising:

(a) a hollow, elongated flexible tube having an axial passage, the tube having a proximal section, a distal section, and an intermediate section between the proximal and distal sections, the distal section including a distal end, the tube having a substantially constant outer diameter, a substantially constant inner diameter, and being composed of a material whose composition does not vary along the length of the [carrier] *tube*;

3

(b) radioactive means positioned in a radioactive segment of the distal section of the tube proximate to the distal end, the radioactive means providing sufficient radiation, in an amount *selected within a range* from 0.01 to 100,000 millicuries per centimeter length of the radioactive segment, [that] *to prevent restenosis in said portion of the artery* when the radioactive [portion] *segment* is placed in [the] *said* portion of the [lumen] *artery post-angioplasty* for an exposure time less than 30 minutes[, restenosis in the portion of the lumen is prevents]; and (c) at least three separate stiffening elements immovably and serially located within the tube and extending longitudinally along the axial passage of the tube for differentially stiffening the proximal, intermediate, and distal sections of the tube, the stiffening elements being selected so that the proximal section of the tube is the stiffest section of the tube, the distal section of the tube is the most flexible section of the tube, and the intermediate section of the tube has a stiffness intermediate the stiffness of the proximal section and the stiffness of the distal section so that the distal section can be advanced in transluminal movement to navigate tortuous turns in the [lumen] *artery* by pushing on the proximal section without crimping the tube.

14. The device of claim 11 wherein each stiffening element has substantially the same flexibility along its *individual* length.

15. The device of claim 11 wherein the radioactive means comprises a plurality of radioactive beads in the radioactive segment of the tube, the beads being sufficiently spaced apart from each other that the radioactive segment is sufficiently flexible to navigate tortuous turns in the [lumen *artery* by pushing on the proximal section without crimping of the tube, the stiffening element in the distal section of the tube not extending into the radioactive segment.

17. A device for endoluminal radiation treatment of a *selected* portion of [a] *an artery* lumen in human beings *after angioplasty in said portion*, the device comprising:

(a) a hollow elongated flexible tube of outer diameter of less than about 1 mm, the tube having a proximal section, a distal section and an intermediate section between the proximal and distal sections, the distal section including a distal end;

(b) a plurality of radioactive beads positioned in a radioactive segment within the distal section of the tube proximate to the distal end of the tube, the radioactive beads providing sufficient radiation in an amount *selected within a range* from 0.01 to 100,000 millicuries per centimeter length of the radioactive segment, such that when the radioactive segment is placed in [a] *the* selected portion of a human *artery* lumen for less than 30 minutes, restenosis in the selected portion of lumen is prevented;

(c) at least three separate stiffening elements immovably and serially located within the tube and extending longitudinally along the axial passage of the tube for differentially stiffening sections of the tube, the stiffening elements comprising a proximal stiffening element in a proximal section of the tube, a distal stiffening element in a distal section of the tube, and an intermediate stiffening element in an intermediate section of the tube between the distal and proximal sections, wherein the proximal stiffening element is the stiffest stiffening element, the distal stiffening element is the least stiff stiffening element, and the intermediate stiffening element has a stiffness intermediate the stiffness of the proximal and distal stiffening elements;

4

(d) means for maintaining *the* radioactive beads spaced apart from each other so that the radioactive segment of the tube is flexible; and wherein the distal stiffening element is sufficiently flexible and the beads are sufficiently spaced apart from each other that the distal section *with the radioactive segment therein* can be advanced in transluminal movement to navigate tortuous turns in the *artery* lumen by pushing on the proximal section without crimping the tube [and that the radioactive segment of the tube can navigate tortuous turns in the lumen].

19. The device of claim [11] 15 or 17 wherein the radioactive beads are spaced [part] *apart* by about 1 mm.

20. The device of claim 17 wherein the total activity of the radioactive beads is *an amount selected within a range from* about 50 to about 500 millicuries per centimeter of length of the radioactive segment.

22. The device of claim [11] 15 or 17 wherein the length of the distal stiffening element in the distal section of the tube terminates proximally to the position of the radioactive beads.

23. The device of claim 11 or 17 wherein the distal section is sufficiently flexible *and of sufficiently small diameter* that the radioactive segment can enter [the] *a* human coronary artery.

24. A method for preventing [stenosis] *restenosis* of a selected [portion] *section* of [a lumen] *an artery* in a [mammal] *human*, comprising the steps of:

(a) *subjecting the selected section to angioplasty for luminal enlargement thereof;*

[(a)] (b) introducing a flexible, elongated carrier having a radioactive segment carrying radioactive elements *through the human vascular system and* into the [lumen] *selected section of the artery* so that the radioactive elements are in the selected section of the [lumen] *artery*;

[(b)] (c) irradiating the selected section of [lumen] *artery* with the radioactive elements for no more than about 45 minutes, the amount of readiation delivered to the selected section of [lumen] *artery* being *a sufficient amount, and* at least about 25 rads per cm length of the selected section of the [lumen] *artery, to prevent restenosis*; and

[(c)] (d) *after irradiating*, withdrawing the carrier *from the artery*.

25. The method of claim 24 wherein at least about 100 rads per cm length of the selected section of the [lumen] *artery* are delivered.

27. The method of claim 24 wherein the amount of radiation delivered is up to about 2500 rads per centimeter length of the selected section of the [lumen] *artery*.

29. A method for enlarging the luminal cross-section of a selected portion of a mammalian *vascular* lumen and preventing [stenosis] *restenosis* of a enlarged portion, the method comprising the steps of:

(a) enlarging the selected portion of the lumen with an endoluminal treatment apparatus having an outer diameter sufficiently small that the apparatus fits in the lumen;

(b) inserting a device having a radioactive segment comprising radioactive means into the enlarged portion of the lumen so that the radioactive means is proximate to the enlarged portion of the lumen;

(c) leaving the device in the lumen with the radioactive means proximate to the enlarged portion of the lumen for internally [radiating] *irradiating* the enlarged portion of the lumen with sufficient radioactivity in an amount *selected within a range* from about 25 to about 2500 rads per centimeter length of the radioactive segment to prevent [stenosis] *restenosis* of the enlarged lumen portion; and (d) thereafter withdrawing the device from the lumen.

30. The method of claim 29 wherein the step of leaving the device in the lumen comprises [radiation] *irradiating* the enlarged portion for less than about 30 minutes.

31. The method of claim [31] *30* wherein the lumen comprises a section of the vasculature of a human.

32. The method of claim 29 wherein the [section of the vasculature] *selected portion of vascular lumen is in* a coronary artery.

34. The method of claim 29 wherein the device comprises:

an elongated, flexible carrier having a proximal section and a distal section, *the distal section comprising the radioactive segment*; and wherein the radioactive means is positioned in [a] *the* radioactive segment of the distal section of the carrier, the radioactive means providing *a selected amount of radiation within a range* from about 0.01 to 100,000 millicuries per centimeter length of the radioactive [segments] *segment*.

35. The method of claim 29 wherein the device provides *a selected amount of radiation in a rate range* from about 100 to about 1000 rads per hour per centimeter length of radioactive segment measured at 3 mm from the outer circumferential surface of the device.

39. The method of claim 29 wherein the step of leaving the device in the lumen comprises leaving the device in the lumen a sufficient time to deliver *a selected amount of radiation within a range* from about 100 to 1000 rads per centimeter length of the enlarged lumen.

42. *A device suitable for endoluminal radiation treatment of a portion of a coronary artery in humans after angioplasty, the device comprising:*

*(a) an elongated, flexible tubular carrier having a proximal section and a distal section; and*

*(b) radioactive means positioned in a radioactive segment of the distal section of the carrier, the radioactive means providing radiation in an amount selected within a range from 0.01 to 100,000 mullicuries per centimeter length of the radioactive segment, wherein the carrier is sized and has sufficient stiffness and flexibility to navigate a vascular system to the human coronary artery so that the radioactive segment can be placed in a selected portion of the coronary artery, and wherein the device has sufficient radioactive means that when the radioactive segment is so placed the radioactive means provides sufficient radiation in less than 30 minutes to prevent restenosis in the selected portion of the coronary artery after subjection thereof to angioplasty.*

43. *The device of claim 42 wherein the radioactive means provides an amount of radiation selected in a range from about 50 to about 500 millicuries per centimeter length of the radioactive segment.*

44. *The device of claim 42 wherein the radioactive means provides a selected amount of radiation in a rate range from about 100 to about 10,000 rads per hour measured at a distance of 3 millimeters from the longitudinal central axis of the carrier.*

45. *The device of claim 42 wherein the radioactive means provides a selected amount of radiation in a rate range from about 500 to about 5000 rads per hour measured at a distance of 3 millimeters from the longitudinal central axis of the carrier.*

46. *A device for the endoluminal radiation treatment of a portion of a coronary artery after angioplasty in humans, the device comprising:*

*(a) an elongated, flexible carrier having a proximal section and a distal section; and*

*(b) radioactive means positioned in a radioactive segment of the distal section of the carrier, the radioactive means providing radiation in an amount selected within a range from 0.01 to 100,000 millicuries per centimeter length of the radioactive segment, wherein the carrier is sized and has sufficient proximal section stiffness and less distal section stiffness relative to the proximal section stiffness to navigate a vascular system to the human coronary artery so that the radioactive segment can be placed in a selected portion of the human coronary artery, and wherein the device has sufficient radioactive means that when the radioactive segment is so placed the radioactive means provides sufficient radiation in less than 30 minutes to prevent restenosis in the selected portion of the coronary artery after subjection thereof to angioplasty.*

47. *The device of claim 1, 5, 11, or 46, wherein the radioactive means comprises a plurality of radioactive pellets in said segment of the carrier.*

48. *The device of claim 1, 5, 11, or 46, wherein the radioactive means comprises radioactive solid material in said segment of the carrier.*

49. *The device of claim 1, 5, 11, or 46, wherein the radioactive means comprises a radioactive liquid in said segment of the carrier.*

50. *The device of claim 1, 5, 11, or 46, wherein the radioactive means comprises a radioactive gas in said segment of the carrier.*

51. *The device of claim 1, 5, 11, or 46, wherein the radioactive means comprises a radioactive powder in said segment of the carrier.*

52. *A device suitable for endoluminal radiation treatment of a portion of a coronary artery angioplasty in humans, the device comprising:*

*(a) an elongated, flexible catheter having a proximal section and a distal section; and*

*(b) radioactive pellets positioned in a radioactive segment of the distal section of the catheter,*

*the radioactive pellets providing radiation in an amount selected within a range from 0.01 to 100,000 millicuries per centimeter length of the radioactive segment,*

*wherein the catheter is sized and has sufficient stiffness and flexibility to navigate the vascular system to a human coronary artery so that the radioactive segment can be placed in a selected portion of the human coronary artery,*

*the radioactive pellets when so placed providing sufficient radiation in less than 30 minutes to prevent restenosis in the selected portion of the coronary artery after subjection thereof to angioplasty.*

53. *A device suitable for endoluminal radiation treatment of a portion of a coronary artery after angioplasty in humans, the device comprising:*

*(a) an elongated, flexible carrier having a proximal section and a distal section; and*

*(b) radioactive means positioned in a radioactive segment of the distal section of the carrier,*

*the radioactive means providing radiation in an amount selected within a range from 0.01 to 100,000 millicuries per centimeter length of the radioactive segment,* wherein the carrier is sized and has sufficient stiffness and flexibility, and wherein the distal section has greater flexibility than the proximal section and the proximal section has greater stiffness than the distal section so that the carrier can navigate the vascular system to a human coronary artery so that the radioactive segment can be placed in a selected portion of the human coronary artery, the radioactive means when so placed providing sufficient radiation in less than 30 minutes to prevent restenosis in the selected portion of the coronary artery after subjection thereof to angioplasty.

54. A method for preventing restenosis of a selected section of a coronary artery lumen in a human, comprising the steps of:

(a) enlarging the selected section of coronary artery lumen;

(b) soon after enlarging the lumen, introducing a flexible, elongated carrier having a distal segment carrying and delivering radioactive elements, through the human vascular system and into the enlarged section of lumen of the coronary artery, for placing the radioactive elements in the coronary artery proximate to the enlarged section of lumen thereof so that the radioactive elements will deliver radioactivity to endoluminal wall of the enlarged section;

(c) irradiating the enlarged section endoluminal wall with the radioactive elements for no more than about 45 minutes, to deliver a sufficient amount of radioactivity to the enlarged section endoluminal wall, amounting to at least about 25 rads per centimeter length of the enlarged section of the coronary artery, to prevent restenosis along the enlarged section endoluminal wall; and (d) after delivering radioactivity of sufficient amount, withdrawing the carrier from the coronary artery.

55. The method of claim 54 wherein the step of introducing the carrier is performed within about 10 minutes after enlarging the selected section of the coronary artery lumen.

56. A method for preventing restenosis of a selected section of an artery in a human, comprising the steps of:

(a) introducing a flexible, elongated carrier having a radioactive segment carrying radioactive elements through the human vascular system and into the selected section of the artery so that the radioactive elements are in the selected section of the artery;

(b) irradiating the selected section of artery with the radioactive elements for no more than about 45 minutes, the amount of radiation delivered to the selected section of artery being a sufficient amount, and at least about 25 rads per cm length of the selected section of the artery, to prevent restenosis; and (c) after irradiating, withdrawing the carrier from the artery.

57. A method for preventing stenosis of a selected section of an artery in a human, comprising the steps of:

(a) introducing a flexible elongated carrier having a radioactive segment carrying radioactive elements through the human vascular system and into the selected section of the artery so that the radioactive elements are in the selected section of the artery;

(b) irradiating the selected section of artery with the radioactive elements for no more than about 45 minutes, the amount of radiation delivered to the selected section of artery being a sufficient amount, and at least about 25 rads per cm length of the selected section of the artery, to prevent stenosis; and (c) after irradiating, withdrawing the carrier from the artery.

58. A method for enlarging the luminal cross-section of a selected portion of a mammalian vascular lumen and preventing stenosis of the enlarged portion, the method comprising the steps of:

(a) enlarging the selected portion of the lumen with an endoluminal treatment apparatus having an outer diameter sufficiently small that the apparatus fits in the lumen;

(b) inserting a device having a radioactive segment comprising radioactive means into the enlarged portion of the lumen so that the radioactive means is proximate to the enlarged portion of the lumen;

(c) leaving the device in the lumen with the radioactive means proximate to the enlarged portion of the lumen for internally irradiating the enlarged portion of the lumen with sufficient radioactivity in an amount selected within a range from about 25 to about 2500 rads per centimeter length of the radioactive segment to prevent stenosis of the enlarged lumen portion; and (d) thereafter withdrawing the device from the lumen.

59. The method of claims 24, 56 or 57, wherein the radioactive elements include radioactive pellets.

60. The method of claims 29 or 58, wherein the radioactive means include radioactive pellets.

61. The method of claims 24, 56, or 57, wherein the radioactive elements are selected from the group of radioactive elements consisting of radioactive solids, radioactive pellets, radioactive beads, radioactive liquids, radioactive gases, and radioactive powders.

62. The method of claims 29 or 58, wherein the radioactive means is selected from the group of radioactive means consisting of radioactive solids, radioactive pellets, radioactive beads, radioactive liquids, radioactive gases, and radioactive powders.

63. The device of claims 1, 5, 42, 46, or 53, wherein the carrier is formed from a metal.

64. The device of claims 11 or 17, wherein the tube is formed from a metal.

64. The device of claim 52, wherein the catheter is formed from a metal.

* * * * *